US006923777B2

(12) United States Patent
Garon

(10) Patent No.: US 6,923,777 B2
(45) Date of Patent: Aug. 2, 2005

(54) BANDAGE COOLING APPARATUS AND METHOD OF USING SAME

(75) Inventor: Mark Garon, St-Hyacinthe (CA)

(73) Assignee: Multivet International Inc., St-Hyacinthe (CA)

( * ) Notice: Subject to any disclaimer, the term of this patent is extended or adjusted under 35 U.S.C. 154(b) by 111 days.

(21) Appl. No.: 10/674,384

(22) Filed: Oct. 1, 2003

(65) Prior Publication Data

US 2005/0075592 A1 Apr. 7, 2005

(51) Int. Cl.[7] ............................. A61F 5/00; A61F 7/00
(52) U.S. Cl. ............................. 602/2; 607/96; 607/114
(58) Field of Search ............................. 602/2; 607/114, 607/96

(56) References Cited

U.S. PATENT DOCUMENTS

| | | | | | |
|---|---|---|---|---|---|
| 2,256,227 A | * | 9/1941 | Zaccheo | ...................... | 118/123 |
| 2,648,108 A | * | 8/1953 | Pentz | ...................... | 422/297 |
| 3,871,381 A | * | 3/1975 | Roslonski | ...................... | 607/104 |
| 3,905,367 A | * | 9/1975 | Dapcich | ...................... | 604/293 |
| 4,331,151 A | * | 5/1982 | Golden | ...................... | 607/105 |
| 4,741,176 A | * | 5/1988 | Johnson et al. | ........... | 62/457.4 |
| 4,793,149 A | * | 12/1988 | Riche | ...................... | 62/293 |
| 4,962,761 A | * | 10/1990 | Golden | ...................... | 607/104 |
| 5,111,810 A | * | 5/1992 | Fortney | ...................... | 607/108 |
| 5,449,379 A | * | 9/1995 | Hadtke | ...................... | 607/107 |
| 5,730,721 A | * | 3/1998 | Hyatt et al. | ................. | 604/500 |
| 5,871,526 A | * | 2/1999 | Gibbs et al. | ................ | 607/104 |

* cited by examiner

Primary Examiner—Henry Bennett
Assistant Examiner—Dinnatia Doster-Greene
(74) Attorney, Agent, or Firm—Robert Brouillette

(57) ABSTRACT

A bandage cooling apparatus has a bandage, a container, a casing, a valve and an actuator. The bandage has a first temperature. The container contains a gaseous fluid and has an exit. The casing comprises a chamber which contains the bandage, an inlet and outlet which both defines passages from the chamber and through the casing. The outlet has a removable lid. The valve connects the inlet of the casing to the exit of the container. The actuator operates the valve whereby a portion of the gaseous fluid expands from the container into the chamber through the valve upon operation of the actuator such that the bandage gets to a second temperature which is different from the first temperature.

37 Claims, 6 Drawing Sheets

FIG_1

BANDAGE COOLING APPARATUS AND METHOD OF USING SAME

FIELD OF THE INVENTION

The present invention concerns a portable bandage apparatus which more particularly provides a cooled bandage by a contact with a gaseous fluid.

BACKGROUND OF THE INVENTION

Many types of body injuries are easily treatable with specialized equipments which are adapted to various body parts, such as shoulders, wrists, knees, etc. The type of injury, the frequency and the duration of treatment influence the conditions under which a selected treatment must be conducted to heal, soothe discomforts or protect a sensitive area of the body.

The Merck Manual of Medical Information states that the immediate treatment of certain types of injuries such as sprains requires Rest, Ice, Compression and Elevation (RICE). Although Rest and Elevation can be attained without any special tool or apparatus, the cold treatment (Ice) and Compression aspect are usually obtained by the use of devices.

Several methods are known to obtain a cold bandage. The first of these is a cold compress made of 2 separate chemical reactants kept apart by 2 polyethylene chambers contained within a polyethylene pouch. By rupturing the chambers within the pouch, the 2 chemical components come into contact of each other creating an endothermic reaction requiring the absorption of heat from it's immediate environment, in this case the injured person. This process however has limited efficacy since the endothermic reaction is not energetically efficient enough to create a cold pouch of reasonable size to be ergonomically feasible within a single pouch. This system requires the use of more than one pouch for one injury. Other drawbacks include the fact that the chemical reaction is not reversible thereby eliminating the possibility of regenerating the pouch so that as a throwaway item it becomes economically and environmentally unfeasible to ergonomically design the pouch for comfort and maximum contact to the injured part. Thus the compression aspect of RICE is not attained efficiently.

A second system exists which though more efficient for the cold and compression aspects of RICE are not as mobile as the previous methods. They are ergonomically designed bandages that contain gels and other substances within pouches that require freezing. They can retain their coldness for a limited amount of time and eventually returning to room temperature. This means that the access to a freezer appliance, whether portable or fixed, is required and therefore greatly reduces practicality and mobility.

Another known system includes a mechanism that circulates cold water within a bandage. This system is also large and of limited mobility. There also exist some bandages that are cooled a little below room temperature through evaporative cooling which have limited therapeutic value in regard to cold treatment.

There is therefore a need for a bandage which efficiently incorporates the benefits associated with the use of the temperature therapy in the healing process of injured body parts.

There is also a need for bandage cooling apparatus which is portable, compact, reusable and easy to carry.

SUMMARY OF THE INVENTION

The object of this invention is to provide a bandage cooling apparatus which efficiently incorporates the benefits associated with the use of the temperature therapy in the healing process of injured body parts, while preferably remaining portable, compact and reusable.

The bandage cooling apparatus of the present invention includes a container such as an aerosol can which contains a gaseous fluid under pressure. Upon operation of the apparatus involving an actuator, the gas expends in a chamber inside the casing where a bandage is located.

The casing includes a lid or a dispensing outlet to remove the bandage from the apparatus once it has been cooled and may then be directly positioned on the injured body part.

There is therefore provided bandage cooling apparatus comprising:
 a) a bandage having a first temperature;
 b) a container containing a gaseous fluid and having an exit;
 c) a casing comprising a chamber which contains said bandage, an inlet and outlet which both define passages from said chamber and through said casing, said outlet having a removable lid;
 d) a valve connecting said inlet of said casing to said exit of said container;
 e) an actuator to operate said valve;
whereby a portion of said gaseous fluid expands from said container into said chamber through said valve upon operation of said actuator, such that said bandage gets to a second temperature which is different from said first temperature.

There is furthermore provided a method for using a bandage cooling apparatus which includes a hollow casing containing a bandage and connected to a container which contains a gaseous fluid, said container being operated by an actuator such that said gaseous fluid is released from said container inside said casing, comprising the steps of:
 a) operation of said actuator;
 b) emission of said gaseous fluid inside said casing;
 c) change of temperature of said bandage.

There is furthermore provided a bandage cooling apparatus for cooling a bandage from a first temperature to a second, lower temperature comprising:
 a) a container containing a gaseous fluid and having an outlet;
 b) a casing comprising a chamber configured and sized to receive the bandage to be cooled, an inlet and outlet that both define passages from said chamber and through said casing, said outlet having a removable lid;
 c) a valve connecting said inlet of said casing to said outlet of said container;
whereby a portion of said gaseous fluid expands from said container into said chamber through said valve, such that the bandage gets to the second temperature.

Other aspects and many of the attendant advantages will be more readily appreciated as the same becomes better understood by reference to the following detailed description and considered in connection with the accompanying drawings in which like reference symbols designated like elements throughout the figures.

The features of the present invention which are believed to be novel are set forth with particularity in the appended claims.

DETAILED DESCRIPTION OF A PREFERRED EMBODIMENT

The objectives of the invention are to provide a bandage cooling apparatus which efficiently incorporates the benefits associated with the use of the temperature therapy in the healing process of injured body parts, while preferably remaining portable, compact and reusable.

Figure 1:
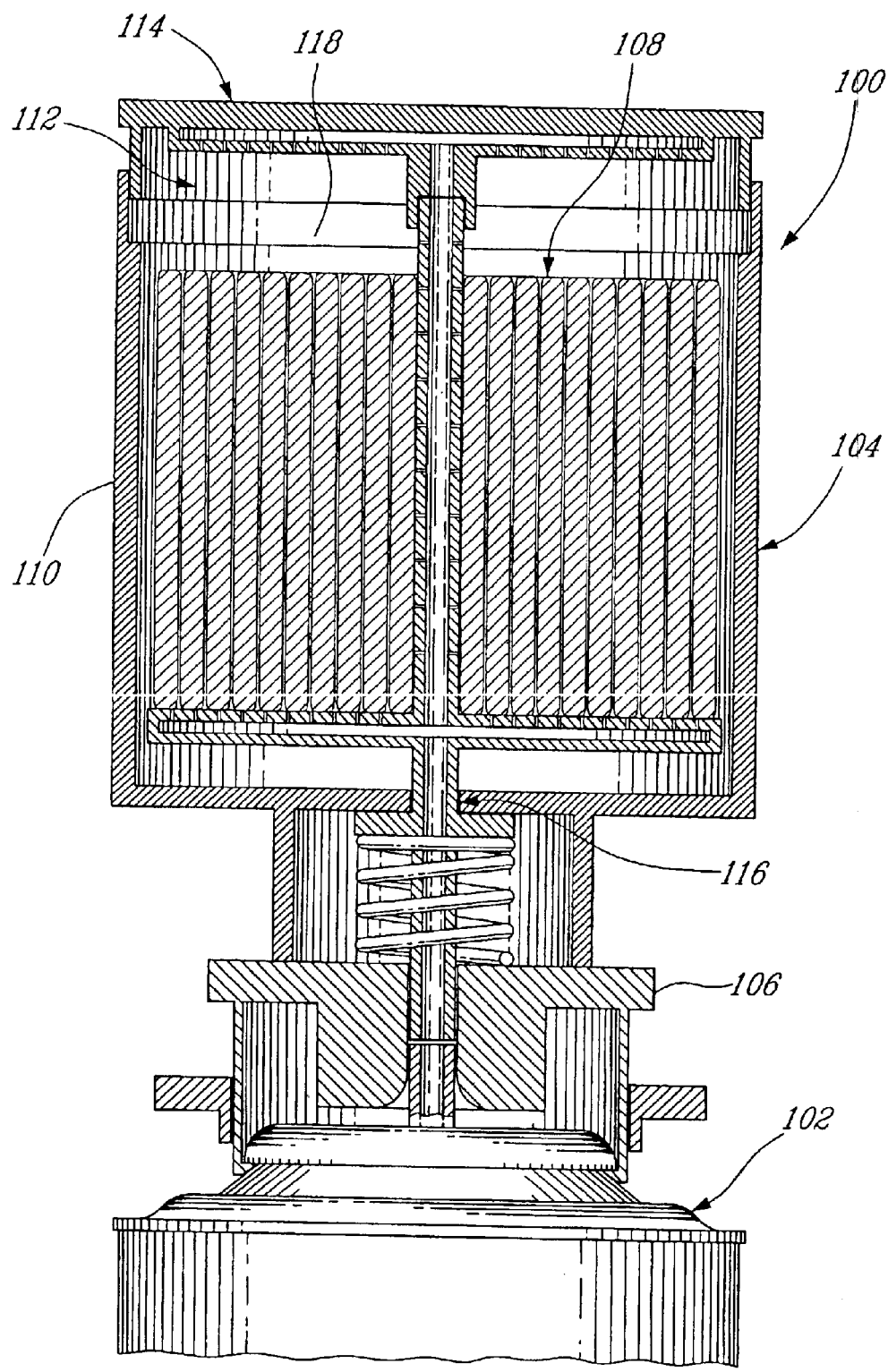
FIG. 1 is a side section view showing a bandage cooling apparatus according to the present invention.

A bandage cooling apparatus 100 is shown in more details in FIG. 1. The apparatus 100 includes a container such as an aerosol can 102 containing a gaseous fluid, a casing 104 including a mount structure 106 which fixedly connects the casing 104 to the aerosol can 102, and a bandage 108. The casing 104 can be connected to the can 102 via the mount structure 106 by any known fixation method, by screw valve actuators or other fixation schemes.

The casing 104 can be of any size or shape, depending on the preferred type of bandage to be cooled. Preferably, the bandage 108 is put in the casing 104 in a rolled form, such that the casing 104 is also preferably a cylindrical hollow body 110. The casing 104 includes an outlet 112 which is preferably covered by a removable lid 114 and an inlet 116 which provides an entrance for the compressed fluid coming from the can 102 or for any gas actuation system providing gas in the apparatus 100. Among other things, the removable lid 114 allows the insertion and the removal of the bandage 108 in and out of the apparatus 100.

The hollow body 110 and the removable lid 114 altogether define an enclosed chamber 118 where the bandage 108 is located and where a volume of atmosphere is provided to permit to a fluid to disperse in the chamber 118.

Figure 2:
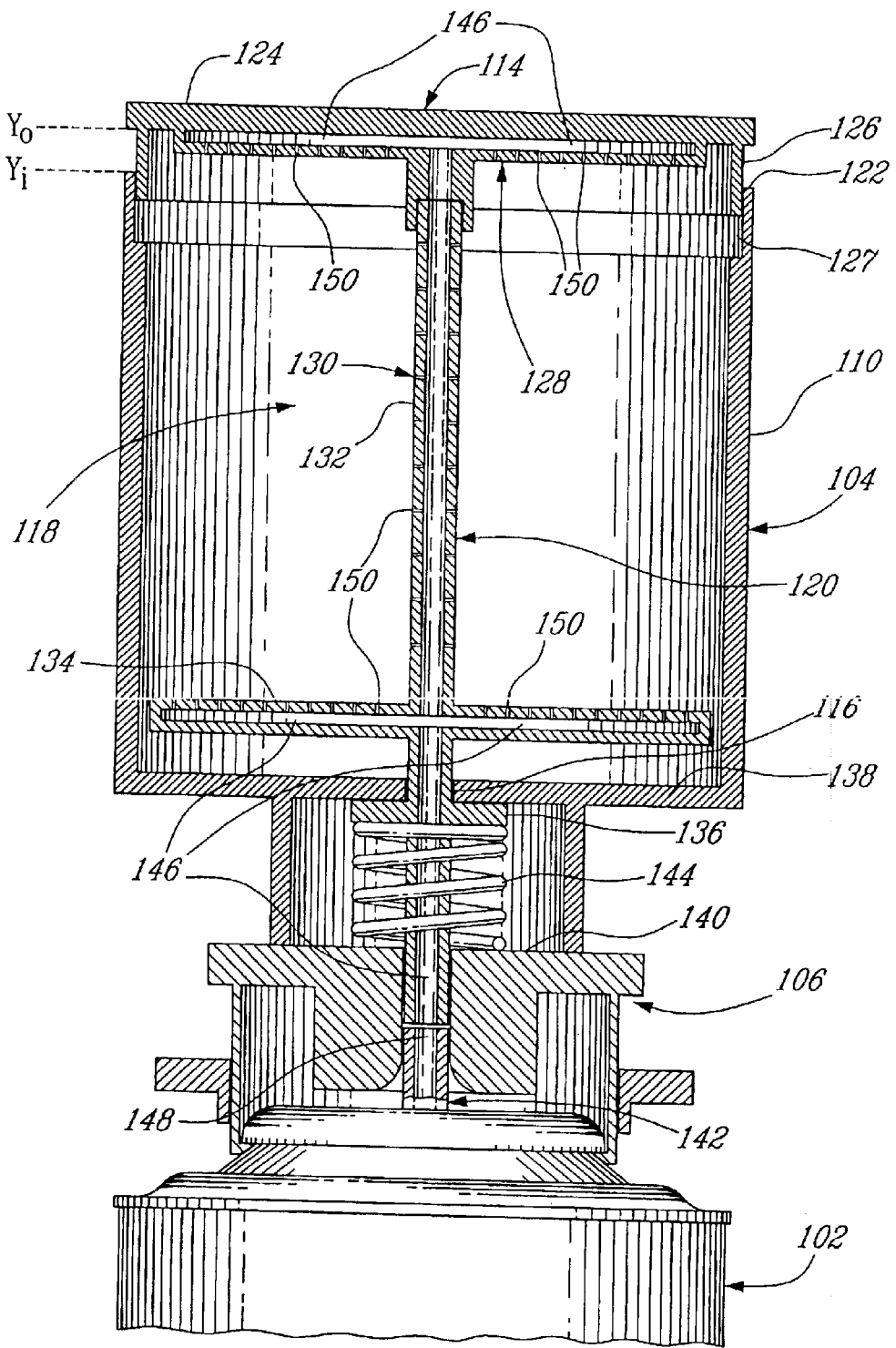
FIG. 2 is a side section view showing the actuation system of the apparatus shown in FIG. 1.

FIG. 2 shows in more details a gas actuation system 120 which may be added to provide gas inside the chamber 118. In this embodiment, the removable lid 114 is mounted near the top 122 of the casing 104 and includes a base 124 and walls 126. The walls 126 define a peripheral shape which cooperates with a peripheral recess 127 in the casing's body 110, therefore providing the apparatus 100 with sliding means. The walls 126 and the recess 127 can be of any size or shape, as long as they complement each other such that one can move in cooperation with each other and one relative to the other.

The base 124 supports a pusher 128 which protrudes inwardly in the chamber 118 and cooperates with a plunger 130. The plunger 130 has at least one member 132 which generally extends along the sliding direction of the walls 126 and recess 127 through the inlet 116, a support 134 onto which the bandage 108 is positioned and a shoulder 136 which regulates the sliding amplitude of the plunger 130 in between the bottom 138 of the body 110 and a stopping surface 140 on the mount 106.

The member 132 extends from the pusher 128 to the valve system 142 of the can 102 such that, when the lid 114 is manually compressed or actuated along the sliding direction from a first position $Y_o$ to a second position $Y_i$, the pusher 128 actuates the valve system 142. At that time, the can's compressed gas is released to the chamber 118 via the casing's 104 inlet 116.

Resilient means such as a spring 144 is preferably added to the apparatus 100 in order to allow the gas actuation system 120 to return to its first position $Y_o$ after being actuated. The spring 144 rests on the stopping surface 140 and it is in a "rest mode" when the lid 114 is in its first position $Y_o$. When the lid 114 goes to a position in between $Y_o$ and $Y_i$ which corresponds to an "open mode", the resilient force caused by the compression of the spring 144 by the shoulder 136 acts on the actuation system 120 to push it back to its first position $Y_o$. The first position $Y_o$ is established by the shoulder 136 being maintained in position between the spring 144 and the bottom 138 of the casing 104. Compressed gas is released from the can 102 to the chamber 118 as long as the actuation system 120 is maintained in the "open mode".

Various ways of providing gas from the can 102 to the chamber 118 via an actuation system 120 are possible. In FIG. 2, the pusher 128 and the plunger 130 have hollow bodies defining inner channels 146 which are connected to the exit 148 of the valve system 142. In the open mode, compressed gas goes through the exit 148 of the valve system 142, such that gas may circulate in the channels 146 and reach the chamber 118 by passing trough openings 150.

Preferably, the fluid in the can 102 is a compressed refrigerant, like HFC134a (tetra-fluoro-ethane) or other gaseous refrigerants. The HFC134a refrigerant has good freezing properties, has a low toxicity and it is largely available.

When expanding into an atmosphere such as the one of the chamber 118, the compressed gas extracts heat from its immediate environment, which results in a cooling of the chamber's 118 atmosphere. In the present invention, the atmosphere of the chamber 118 contains the bandage 108 which is therefore cooled when the gas expends in contact with the bandage 108.

By pressing upon the casing 104 on its lid 114, the gas is allowed to circulate around and or through the bandage 108 in the chamber 118. To increase the efficiency of the cooling effect, the bandage 108 must previously be folded or rolled in a configuration that maximizes contact between gas and bandage. Within a few seconds, bandages 108 with lower temperatures can be attained.

Once properly cooled or frozen, the bandage 108 can then be applied to the injured part. In certain instances it is possible to refold the bandages 108 and reposition them in the casing 104 thereby permitting their reusability.

Figure 3:
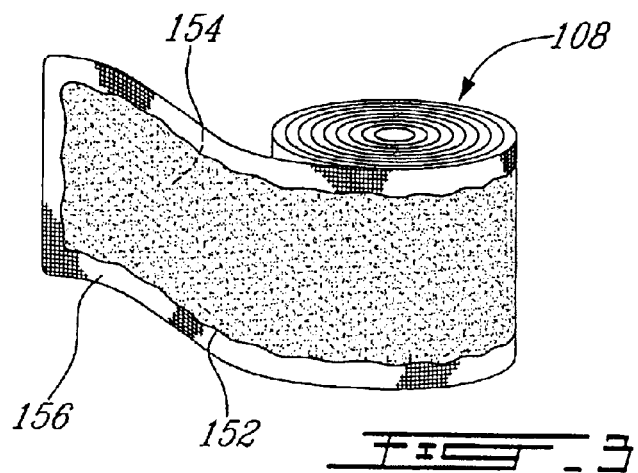
FIG. 3 is an isometric view showing one embodiment of the bandage which can be used in the bandage cooling apparatus shown in FIG. 1.
Figure 4:
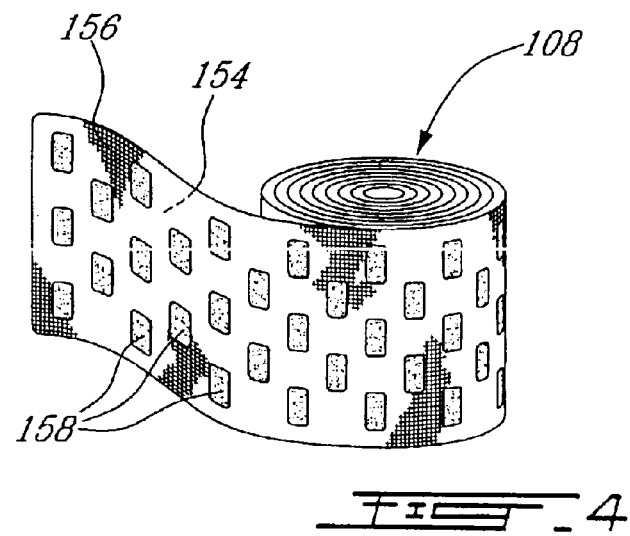
FIG. 4 is an isometric view showing another embodiment of the bandage which can be used in the bandage cooling apparatus shown in FIG. 1.
Figure 5:
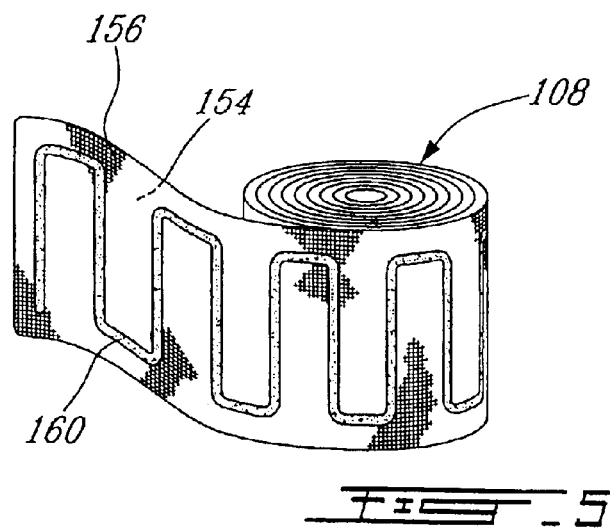
FIG. 5 is an isometric view showing still another embodiment of the bandage which can be used in the bandage cooling apparatus shown in FIG. 1.

In the present invention, the gas expansion occurs in the vicinity or in contact with the bandage 108. As seen in FIGS. 3, 4 and 5, other bandages 108 include a freezable solution or gel 152 such as Poly-vinyl alcohol to increase the efficiency of the cooling effect coming from the gas expansion in the chamber 118. The bandage 108 preferably incorporates humid gel 152 on at least one of its surfaces 154, 156, a plurality of gel containers 158 or a conduit matrix containing gel 160. In those instances, the expending gas extracts its heat from what is in its immediate atmosphere, thereby lowering the gel temperature and thus creating a cold bandage.

The bandage 108 can be a thin textile strip, or hollow mesh containing the gel that can be easily wrapped around the injured limb. The outside covering of the bandage 108 can also contain a material that can control the temperature of the bandage to prevent excessive freezing to avoid frostbite.

It should be noted that such bandages can be of any shape or size (such as pads, small cushioned fabrics, pieces of cloth, etc) and can also be designed with particular body parts in mind: shoulder, wrist, knees, etc. The concept is also not restricted to humans but to any animal that could benefit from such a therapy. It can also be applied to other types of injuries or discomforts other than sprains.

Figure 6:
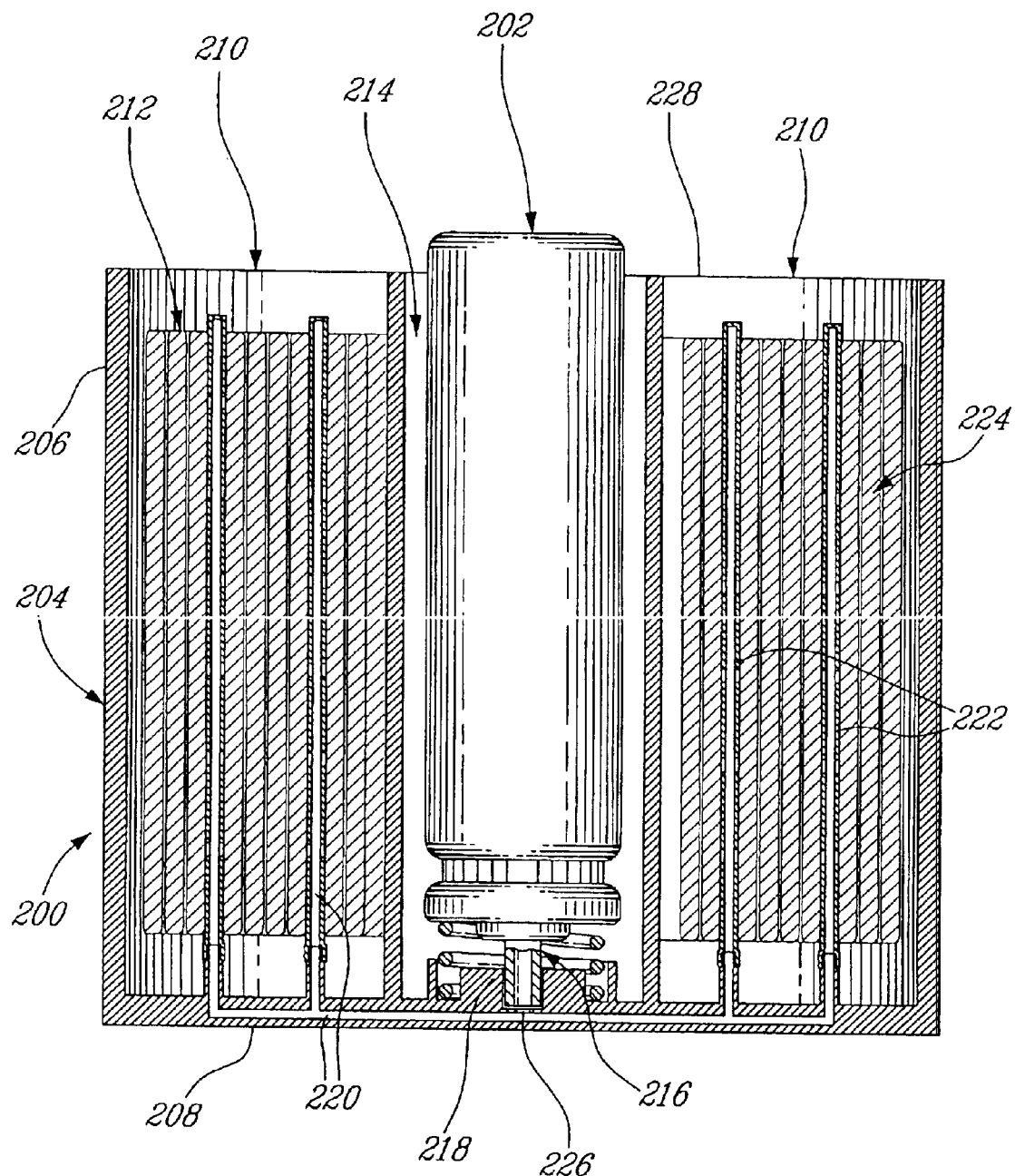
FIG. 6 is a side section view showing another embodiment of the bandage cooling apparatus shown in FIG. 1.

FIG. 6 illustrates another embodiment of the present invention. The portable bandage apparatus 200 includes an aerosol can 202 containing the refrigerant. The can 202 is preferably selected because of its small dimensions which allow it to be almost completely encapsulated within the casing 204. The casing 204 has a preferably cylindrical hollow body 206 with a closed end 208 and an outlet 210 for the insertion and removal of the bandage 212.

In this embodiment, the can 202 is generally fixedly located in a cavity 214 of the body 206, such that its valve 216 engages in the mount structure 218. The mount structure 218 opens to inner channels 220 which first extend in the closed end 208 and then protrude inside arms 222 within the gas chamber 224 where the bandage 212 is located. The arms 222 are preferably configured as straws extending from the closed end 208, but could be made from arc segments (not shown) extending in a generally vertical and radial direction.

The apparatus 200 is operated by directly pressing on the can 202 which has the effect of opening its valve 216, or by pressing on a removable lid (not shown) connected to the can 202, as previously described for the first embodiment. The pressured gas is also released to the chamber 224 the same way which was described hereinabove.

Preferably, layers 226, 228 are added to seal the chamber 224 containing the humid bandage 212 and to ensure its freshness. The thin layer 226 located where the valve 216 connects to the inner channels 220 is destined to be perforated upon insertion of the can 202 or upon its first operation. The other layer 228, such as an aluminum sheet, is preferably manually removed from the casing 204 before operation of the can 202, but can be replaced by the use of a removable lid (not shown).

The apparatus 200 described in this embodiment can be made such that it is partly or completely disposable after one use. In the case where the casing 204 with a fresh bandage 212 is required, any new or partly used can 202 may be adapted to the casing 204. Alternatively, any new can 202 can be installed on a previously used bandage which is put back in the chamber 224.

Figure 7:
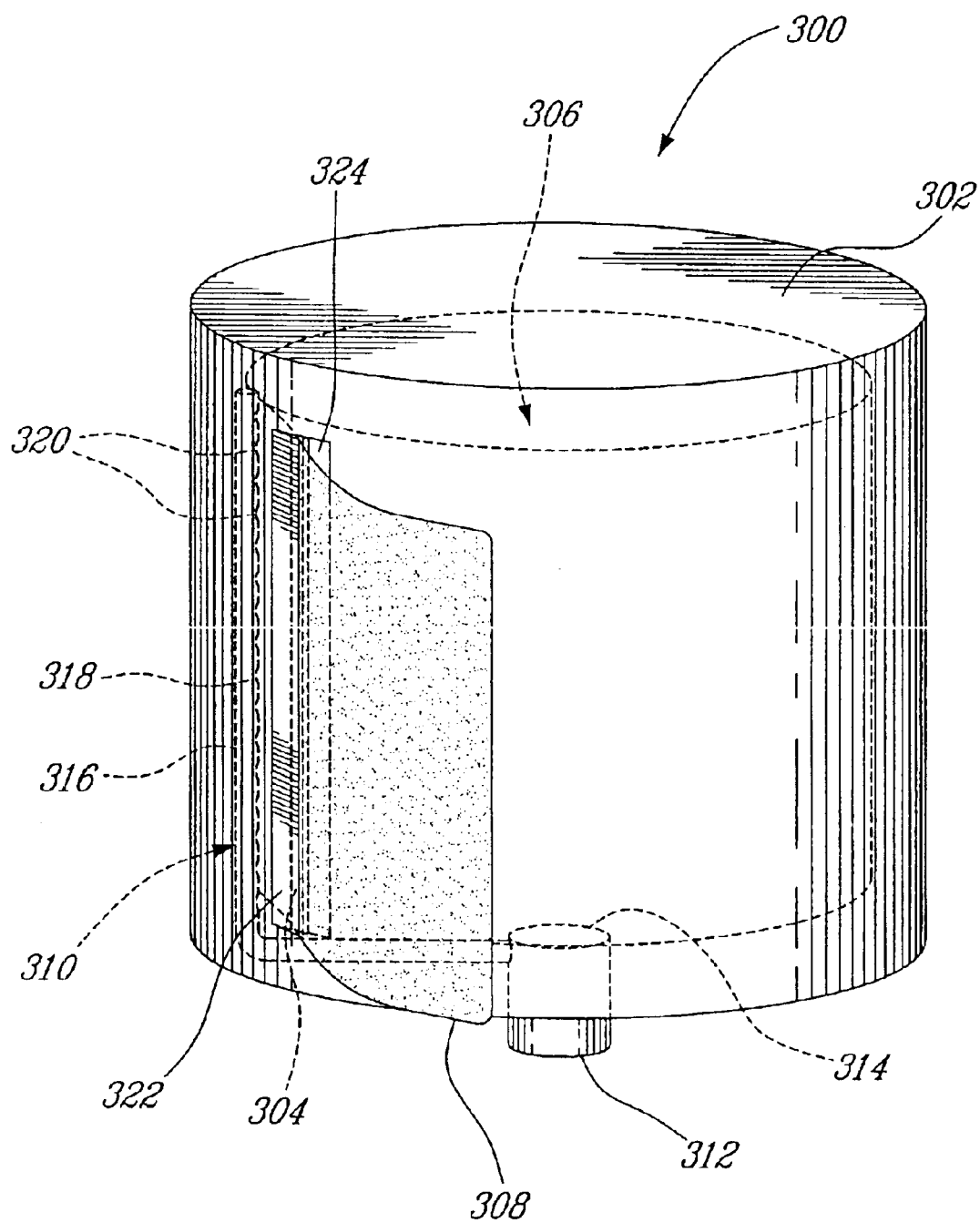
FIG. 7 is an isometric view showing another embodiment of the bandage cooling apparatus according to the present invention.

As shown in FIG. 7, another embodiment of the apparatus 300 incorporates separate locations for the removable lid 302 and a dispensing outlet 304 which are both in communication with the inner chamber 306. Preferably, the removable lid 302 allows the repositioning of a bandage 308 after it has been completely dispensed through the dispensing outlet 304.

The gas actuation system 310 is preferably located near the dispensing outlet 304 such that it allows the expansion of gas near the bandage 308 at the dispensing outlet 304. A valve 312 links the inlet 314 to a compressed fluid container (not shown) such that it maintains the gas actuation system 310 in an "open" mode with gas under pressure in the gas actuation system 310.

The gas actuation system 310 has a hollow member 316 which has one end connected to the inlet 314 and which extends near the dispensing outlet 304. The member 316 defines an inner channel 318 and includes a plurality of openings 320 which open to the chamber 306 and are oriented as to face one of the bandage's 308 surface. When the apparatus 300 is not operated, a movably operated block arm 322 mounted in the chamber 306 extends adjacent to the member 318 and the dispensing outlet 304. The arm 322 acts as a seal and covers the openings 320 from the chamber 306 such that pressured gas in the channel 318 can't be released in the chamber 306.

To operate the gas actuation system 310, the user pulls the bandage 308 out of the apparatus 300 at a specific angle with respect to the dispensing outlet 304 such that the block arm 322 does not cover the openings 320 from the chamber 306 (as illustrated in FIG. 7). Since the gas is maintained under pressure in the channel 318, the removal of the block arm 322 from covering the openings 320 allows the pressured gas to be released in the chamber 306 and therefore on the bandage 208. As the bandage 308 is being pulled out, only a portion of the bandage 308 is cooled as it passes near the dispensing outlet 304.

Further to this, a cutter 324 is also preferably added to cut the length of cooled bandage which is required. To do so, the bandage 308 needs to be in contact with the cutter 324 which is preferably positioned in the vicinity of the dispensing outlet 304.

Figure 8:
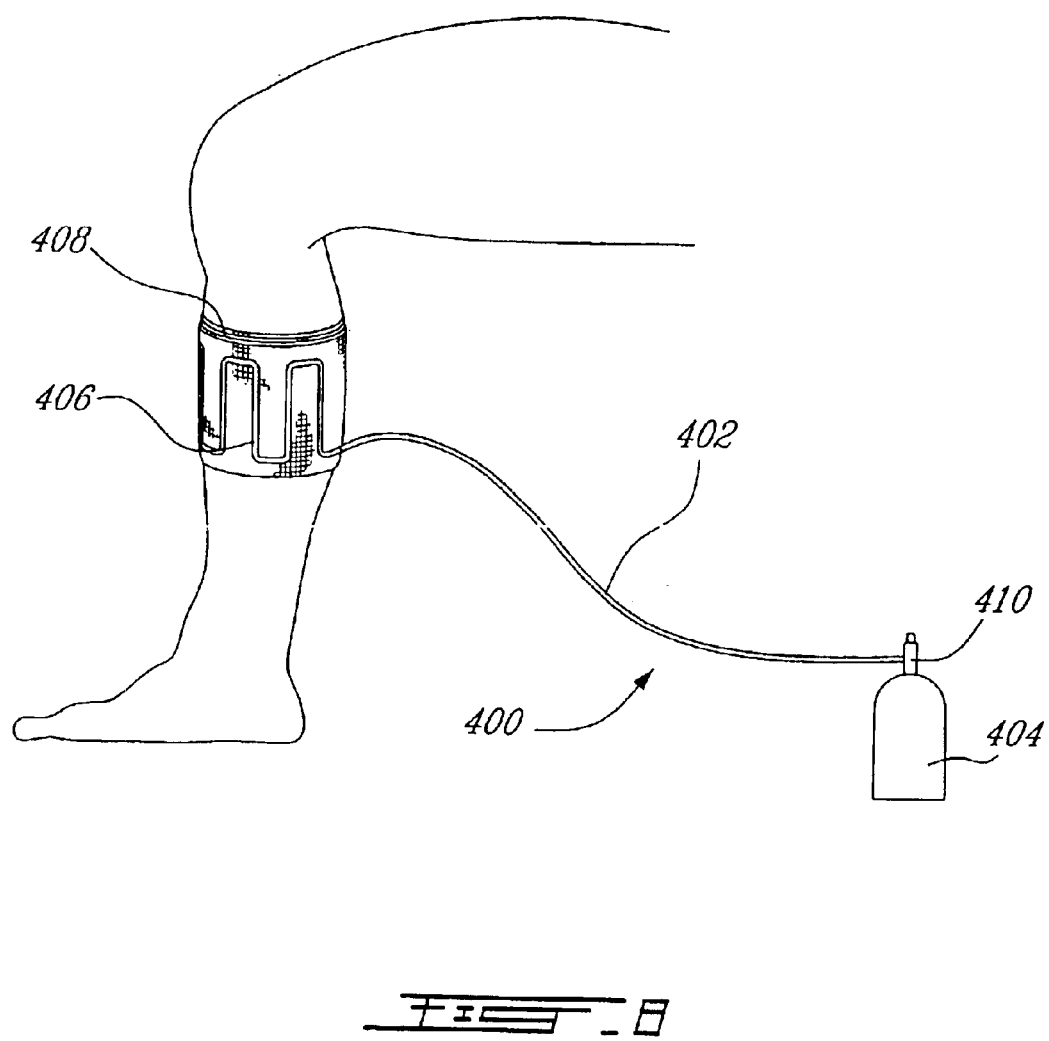
FIG. 8 is an isometric view showing still another embodiment of the bandage cooling apparatus according to the present invention.

Another embodiment shown in FIG. 8 of the apparatus 400 includes a bandage 408 that has a connector tube 402 linking an aerosol can 404 and the conduit matrix 406 through a valve 410. The advantage of this system is that it becomes possible to re-freeze the bandage 408 while wearing it. This embodiment can be manually operated or automatically actuated at a predetermined period of time. It is also possible to incorporate temperature sensors (not shown) near the bandage 408 and a solenoid valve to the apparatus 400 to accurately control the bandage 408 temperature when worn on a body part.

Also, if the aerosol can 404 is small enough, it becomes possible to wear it near the bandage 408. The can 404 size vary from the very small aerosol cans of 30 ml to larger dispensers.

Although preferred embodiments of the invention have been described in detail herein and illustrated in the accompanying figures, it is to be understood that the invention is not limited to these precise embodiments and that various changes and modifications may be effected therein without departing from the scope or spirit of the present invention.

What is claimed is:

1. A bandage cooling apparatus comprising:
   a) a bandage having a first temperature;
   b) a container containing a gaseous fluid and having an exit;
   c) a casing comprising a chamber which contains said bandage, an inlet and outlet which both define passages from said chamber and through said casing, said outlet having a removable lid;
   d) a valve connecting said inlet of said casing to said exit of said container;
   e) an actuator to operate said valve;
   whereby a portion of said gaseous fluid expands from said container into said chamber through said valve upon operation of said actuator, such that said bandage gets to a second temperature which is different from said first temperature.

2. A bandage cooling apparatus as claimed in claim 1, wherein said second temperature is lower than said first temperature.

3. A bandage cooling apparatus as claimed in claim 2, wherein said gaseous fluid is HFC134a (tetra-fluoro-ethane).

4. A bandage cooling apparatus as claimed in claim 1, wherein said container is an aerosol.

5. A bandage cooling apparatus as claimed in claim 1, wherein said actuator is a plunger inside said casing, said plunger being manually operated via said removable lid.

6. A bandage cooling apparatus as claimed in claim 5, wherein said plunger includes inner channels connected to said exit of said valve.

7. A bandage cooling apparatus as claimed in claim 6, wherein said channels are in communication with said chamber through openings on said plunger.

8. A bandage cooling apparatus as claimed in claim 1, wherein said actuator includes temperature sensors to control said valve.

9. A bandage cooling apparatus as claimed in claim 1, wherein said actuator is manually operated.

10. A bandage cooling apparatus as claimed in claim 1, wherein said actuator has a first position and a second position, said apparatus being operated when said actuator moves from said first position to said second position and said actuator being put back to said first position by resilient means after operation of said apparatus.

11. A bandage cooling apparatus as claimed in claim 1, wherein said bandage is disposable.

12. A bandage cooling apparatus as claimed in claim 1, wherein said bandage is reusable.

13. A bandage cooling apparatus as claimed in claim 1, wherein said bandage is rolled in said casing.

14. A bandage cooling apparatus as claimed in claim 13, wherein said casing is cylindrical.

15. A bandage cooling apparatus as claimed in claim 1, wherein said bandage is an elastic compression bandage.

16. A bandage cooling apparatus as claimed in claim 1, wherein said bandage incorporates gel on at least one of its surfaces.

17. A bandage cooling apparatus as claimed in claim 16, wherein said bandage includes a temperature control material on one of its surface.

18. A bandage cooling apparatus as claimed in claim 1, wherein said bandage incorporates a plurality of gel containers.

19. A bandage cooling apparatus as claimed in claim 1, wherein said bandage incorporates a conduit matrix containing gel.

20. A bandage cooling apparatus as claimed in claim 19, wherein said apparatus further comprises a tube between said container and said conduit matrix.

21. A bandage cooling apparatus as claimed in claim 20, wherein said actuator includes at least one temperature sensor to control said valve.

22. A bandage cooling apparatus as claimed in claim 1, wherein said bandage incorporates a temperature controlling gel on at least one of its surfaces.

23. A bandage cooling apparatus as claimed in claim 1, wherein said container is generally fixedly located in a cavity of said casing.

24. A bandage cooling apparatus as claimed in claim 23, wherein said actuator is operated by pressing on said container.

25. A bandage cooling apparatus as claimed in claim 23, wherein said casing contains inner channels connected to said inlet of said casing and in communication with said chamber through holes.

26. A bandage cooling apparatus as claimed in claim 25 wherein said casing further includes arms connected to said inner channel, said arms containing inner channels and holes and protruding in said chamber.

27. A bandage cooling apparatus as claimed in claim 23, wherein said inlet and said outlet of said casing has layers to seal said chamber.

28. A bandage cooling apparatus as claimed in claim 1, wherein said outlet includes a bandage dispensing outlet and a bandage reinsertion outlet.

29. A bandage cooling apparatus as claimed in claim 28, wherein said actuator is located near said bandage dispensing outlet.

30. A bandage cooling apparatus as claimed in claim 29, wherein said actuator is a hollow member having an inner channel in communication with said chamber through a plurality of openings.

31. A bandage cooling apparatus as claimed in claim 30, wherein said openings are oriented toward said bandage.

32. A bandage cooling apparatus as claimed in claim 31, wherein said apparatus comprise an arm having a first position covering said openings and a second position away from said openings.

33. A bandage cooling apparatus as claimed in claim 32, wherein said arm is movably operated by pulling said bandage out of said apparatus.

34. A bandage cooling apparatus as claimed in claim 33, wherein said apparatus further comprises a cutter in the vicinity of said bandage dispensing outlet.

35. A bandage cooling apparatus as claimed in claim 1, wherein said apparatus is portable.

36. A method for using a bandage cooling apparatus which includes a hollow casing containing a bandage and connected to a container which contains a gaseous fluid, said container being operated by an actuator such that said gaseous fluid is released from said container inside said casing, comprising the steps of:
   a) operation of said actuator;
   b) emission of said gaseous fluid inside said casing;
   c) change of temperature of said bandage.

37. A bandage cooling apparatus for cooling a bandage from a first temperature to a second, lower temperature comprising:
   a) a container containing a gaseous fluid and having an outlet;
   b) a casing comprising a chamber configured and sized to receive the bandage to be cooled, an inlet and outlet that both define passages from said chamber and through said casing, said outlet having a removable lid;
   c) a valve connecting said inlet of said casing to said outlet of said container;
   whereby a portion of said gaseous fluid expands from said container into said chamber through said valve, such that the bandage gets to the second temperature.

* * * * *